INOCULANT INJECTOR INSTRUMENT

Original Filed March 2, 1950 3 Sheets-Sheet 1

INVENTORS.
FRANK ZIHERL
BY ARTHUR S. KISH
William Soler
ATTORNEY.

INOCULANT INJECTOR INSTRUMENT

Original Filed March 2, 1950 3 Sheets-Sheet 2

INVENTORS.
FRANK ZIHERL
BY ARTHUR S. KISH
William Solu
ATTORNEY.

INOCULANT INJECTOR INSTRUMENT

Original Filed March 2, 1950 3 Sheets-Sheet 3

INVENTORS.
FRANK ZIHERL
BY ARTHUR S. KISH
William Seler
ATTORNEY.

United States Patent Office

Re. 24,419
Reissued Jan. 21, 1958

24,419

INOCULANT INJECTOR INSTRUMENT

Frank Ziherl, Euclid, and Arthur S. Kish, Mayfield Heights, Ohio, assignors, by mesne assignments, to Geoffrey W. Walker, Frank Ziherl, and Louis A. Ziherl, Cleveland, Ohio Original No. 2,687,724, dated August 31, 1954, Serial No. 147,166, March 2, 1950. Application for reissue August 8, 1955, Serial No. 527,186

19 Claims. (Cl. 128—173)

Matter enclosed in heavy brackets [ ] appears in the original patent but forms no part of this reissue specification; matter printed in italics indicates the additions made by reissue.

The present invention relates generally to instruments used medically for the purpose of injecting inoculant into patients, and more particularly to an instrument for effecting jet or spray inoculation.

Jet or high-pressure spray inoculation is a recently developed medical technique in which medicinal fluids are injected into the body without breakage of the skin, as contrasted to or distinguished from hypodermic injection in which a hollow needle is caused to penetrate the skin and muscle tissue. The injection is accomplished by forcing a very thin stream of fluid through the skin at high pressure. The fluid jet is about .003 inch in diameter, which is approximately the size of a pore in the human skin, and the high velocity of the jet causes it to pass through the skin and diffuse into the muscle tissues.

It is the primary object of our invention to provide an improved instrument or device for effecting the above-described process of jet inoculation.

Another object of our invention is to provide an instrument of the character described, in which hydraulic means are employed to energize a spring-pressed plunger.

Still another object of the invention is to provide an instrument of the character described, which is manually operable and which can develop very high pressure.

Another object of our invention is to provide an instrument of the character described, with self-loading means to permit repeated injection of inoculant with a single ampule.

Still another object of our invention is to provide an inoculant injector instrument having improved means for metering the inoculant which is to be ejected.

A further object of our invention is to provide said instrument with improved means for limiting the stroke of the plunger and thereby controlling the volume of inoculant which is ejected.

A still further object of our invention is to provide an instrument of the character described, wherein means are provided to prevent leakage or drip of the inoculant from the ampule after the injection has been completed.

Other objects and advantages of the invention will be apparent during the course of the following description.

In the accompanying drawings, forming a part of this specification, and in which like numerals are employed to designate like parts throughout the same, Fig. 1 is a front end elevation of an injector instrument embodying the features of our invention.

Figure 2:
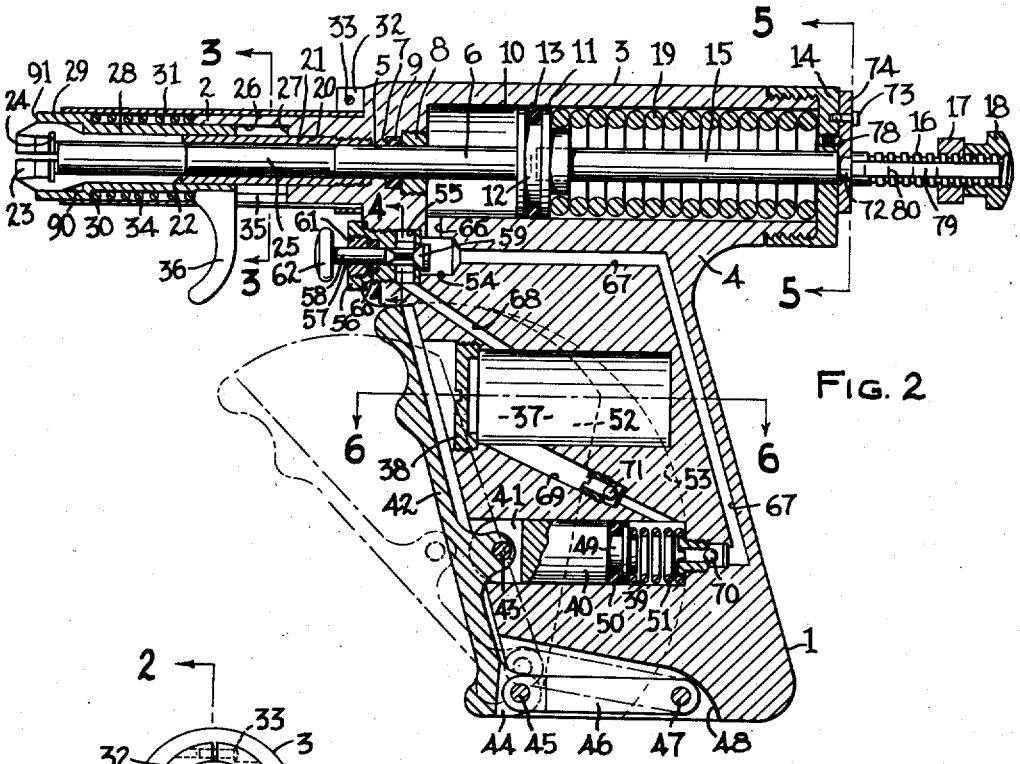
Fig. 2 is a longitudinal cross-sectional view taken on line 2—2 of Fig. 1.
Figure 1:
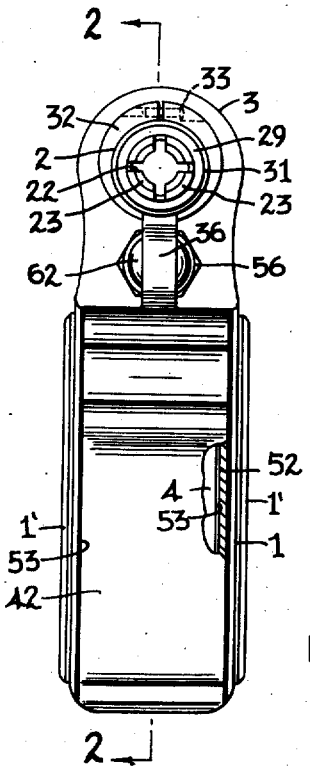
Figure 3:
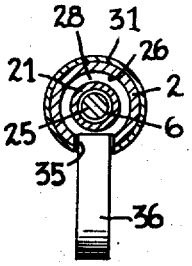
Fig. 3 is a cross-sectional view of the barrel of the instrument taken as indicated by line 3—3 of Fig. 2.

Referring more particularly to Figs. 1 to 6 of the drawings, the injector instrument is seen to have some resemblance to a piston in its overall appearance, and has a grip or butt portion 1, having ornamental side plates 1', a barrel portion 2, and a piston housing 3.

The principal part of the device is a unitary body 4 which may be a casting or formed out of rolled bar stock. The upper portion of the body 4 comprises the barrel 2 and piston housing 3, heretofore referred to, and this upper portion is bored as at 5 to slidably receive a plunger 6. The bore 5 is counterbored to form a shoulder 7 and the counterbore is tapped to receive a threaded follower 8 which serves to compress a resilient sealing ring 9 against the shoulder 7 and thus seal the plunger against leakage.

The bore 5 is additionally counterbored, as viewed from the right of Fig. 2, to form a relatively large compression chamber or cylinder 10 which slidably receives a piston 11 which is secured to or formed integrally with one end of the plunger 6. The piston has a circumferential recess 12 in which is retained a resilient sealing ring 13 which has wiping engagement with the wall of the cavity 10.

The open end of cylinder 10 is closed by means of a cap 14, which is threadedly secured to the exterior of the piston housing 3. The cap is provided with a central aperture to permit the passage therethrough of an extension rod 15, one end of which is threadedly secured to the piston 11.

The major portion of the rod 15, which projects or extends beyond the cap 14, is externally threaded as at 16 and has threadely secured thereto an adjusting nut 17 and a lock nut 18 whose function will be described hereinafter.

Interposed between the piston 11 and the cap 14 is *an actuating element in the form of* a compression coil spring 19 which normally biases the piston to the left as viewed in Fig. 2.

The forepart or barrel portion 2 of the body 4 is bored as at 20 and internally threaded to receive a self-opening collet 21 having a series of longitudinal slots 22 therein which permit the jaws 23 thereof to be converged or contracted into gripping or clamping relationship. The inner face of the jaws 23 has formed thereon an annular groove or recess 24 which, as will more fully appear hereinafter, is adapted to embrace a cartridge C, described hereinafter. *The cartridge C provides a medicament or inoculant chamber carried or mounted on the forward end of the barrel portion 2 of the body 4.* The plunger 6, which has an undercut or clearance portion 25, is slidable within the collet 21.

The bore 20 is counterbored at 26 forming an annular recess which terminates in a shoulder 27. A tubular sleeve 28 which surrounds the collet 21 is slidably received in the annular recess. The sleeve 28 terminates in a radially offset portion 29 which forms an external annular shoulder 30.

The external diameter of the offset portion 29 is the same as the diameter of the barrel portion of the body 4, and both these parts are encased in a sleeve 31 which is clamped to the body 4 by means of a split ring 32 which is contracted by means of an adjusting screw 33.

A compression coil spring 34 is interposed between the shoulder 30 of sleeve 28 and the end of the barrel portion 2 of the body 4. The spring 34 normally biases the sleeve 28 to the left as viewed in Fig. 2.

Both the sleeve 31 and the barrel 2 are provided with a longitudinally extending slot as at 35, this slot being of sufficient width and length to permit reciprocal movement therein of a trigger 36 which is secured, as by brazing, to the sleeve 28. By means of the trigger 36, the sleeve 28 may be manually retracted in opposition to spring 34 thus relieving the jaws 23 of envelopment by the offset portion 29 and permitting them to expand radially.

The butt portion 1 of the body 4 is provided with a cavity 37 which serves as a reservoir for the hydraulic fluid. The reservoir 37 is closed by a threaded cap or cover 38.

The butt 1 is provided with a second cavity 39 which serves as a cylinder in which is slidably mounted a piston 40 having a bifurcated end portion forming ears 41. A suitably formed handle 42 is pivotally connected to the ears 41 of the piston 40 by means of a pin 43, this connection being intermediate the ends of the handle. The lower end 44 of the handle is pivotally secured, as by pin 45, to a link 46, which, in turn, is pivotally secured to the butt 1 by pin 47. The link 46 is concealed within the butt in a recess 48 which is large enough to permit free movement of the link.

The piston 40 is provided with a circumferential recess 49 in which is retained a resilient sealing ring 50 which has wiping engagement with the wall of cylinder 39. A compression coil spring 51 is disposed between the piston 40 and the end of the cylinder 39 and normally urges the piston to the left as viewed in Fig. 2.

The handle 42 is provided with parallel flanged portions or wings 52 which are received in vertical recesses 53 provided in the butt 1 and thus serve to guide the movement of the handle.

The butt 1 is further provided with a cavity or valve by-pass chamber 54 which is counterbored as at 55 to form a valve chamber, and tapped to receive a threaded valve body 56. The valve body, in turn, has a central bore 57 in which is slidably received a valve stem 58 having an enlarged conical end portion 59.

The bore 57 is counterbored and tapped to receive a resilient sealing ring 60 which is retained in position by a threaded follower 61.

A portion of the valve stem 58 projects exteriorly of the body 4 and has secured thereto an enlarged head or button 62 for convenience in effecting manipulation of the valve.

Figure 4:
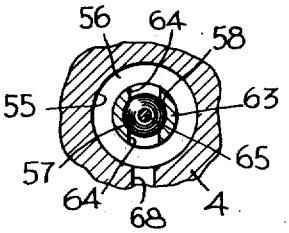
Fig. 4 is an enlarged fragmentary cross-sectional view of the valve structure taken on line 4—4 of Fig. 2.

As best seen in Figs. 2 and 4, the valve body 56 is provided with a portion 63 of reduced diameter, which portion has a plurality of diametrically extending openings 64 provided therein. The valve stem 58 also has a portion 65 of reduced diameter thereby forming a clearance space between the valve stem and the interior wall of the portion 63 of the valve body. The conical end 59 of the valve stem seats on the valve body 56 in sealing engagement with the bore 57.

A channel or passageway 66 interconnects the cylinder 10 with the by-pass chamber 54 and a channel 67 interconnects the by-pass chamber 54 and the cylinder 39. A third channel 68 interconnects the valve chamber 55 and reservoir 37, and another channel 69 interconnects reservoir 37 and cylinder 39. The function of these channels will be described hereinafter.

A ball check valve 70 is mounted in the channel 67, intermediate the cylinder 39 and the by-pass chamber 54, and another ball check valve 71 is mounted in the channel 69, intermediate the reservoir 37 and cylinder 39.

The operation of the instrument will now be described.

As heretofore stated, it is necessary that a high pressure be developed by the plunger 6. To attain this objective, the spring 19 must have a high energization value, for example, 250–300 pounds when fully compressed. It will readily be apparent that in order to cock the plunger, that is, retract it in opposition to the spring 19, a great deal of force or strength would be required. In fact, it would normally be considered an impossibility for the average individual to manually retract the plunger. Therefore, our invention lies in providing *force-compounding* means for effecting retraction of the plunger, which means are readily manually operable by the user of the instrument.

With the plunger 6 extended, that is, with the spring 19 expanded, the reservoir 37 is filled with a suitable hydraulic fluid such as light mineral oil or the like, so that the cylinder 39 and the channels 67 and 69 are substantially filled. After the reservoir 37 has been completely charged with the hydraulic fluid, the reservoir is closed and sealed by means of the cover 38.

The butt portion 1 of the device is now grasped in one hand with the fingers overlying the handle 42, which is normally disposed in the dotted line position shown in Fig. 2, due to the urging of piston spring 51.

The piston 40 is then reciprocated in cylinder 39 by means of the compound pivotal movement of handle 42. The link 46, which permits vertical movement of the handle 42, prevents any lateral strain from being imposed on the piston 40 during pivotal movement of the handle.

As the piston is forced to the right, as viewed in Fig. 2, it forces the fluid through ball valve 70 into channel 67. During this displacement of the fluid, the back pressure in channel 69 causes ball check valve 71 to close, thereby preventing a return flow of the fluid into reservoir 37.

Upon completion of the compression stroke of piston 40, the spring 51 returns the piston to its initial position, and during this movement, the suction or vacuum created in the cylinder 39 causes ball check valve 71 to open, thereby causing an additional flow of fluid from reservoir 37 through channel 69 into cylinder 39. At the same time, the back pressure in channel 67 causes ball check valve 70 to close, thereby preventing any return flow of the fluid from channel 67 into cylinder 39.

As this fluid pump, of which piston 40 is an element, is operated, the fluid is forced through channel 67, through by-pass chamber 54, through channel 66 and into cylinder 10, where it steadily builds up an increasing hydraulic pressure. This pressure, acting on piston 11, forces it to the right, as viewed in Fig. 2, thereby retracting the plunger 6 and further extending the rod 15 beyond cap 14.

The fluid pressure also acts on the exposed surface of the conical portion 59 of valve stem 58 thereby urging the valve stem to the left, as viewed in Fig. 2, and causing the bore 57 to be closed against passage of the fluid.

The fluid pumping operation is repeated several times until the spring 19 has been fully compressed. The plunger 6 is thereby in cocked position.

Figure 5:
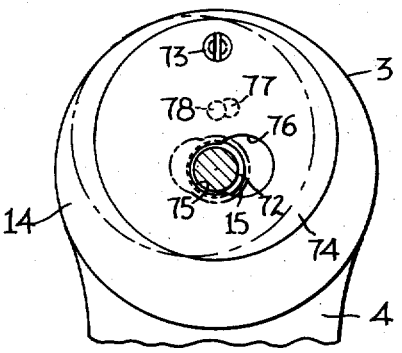
Fig. 5 is an enlarged fragmentary cross-sectional view of the locking device taken as indicated by line 5—5 of Fig. 2.
Figure 6:
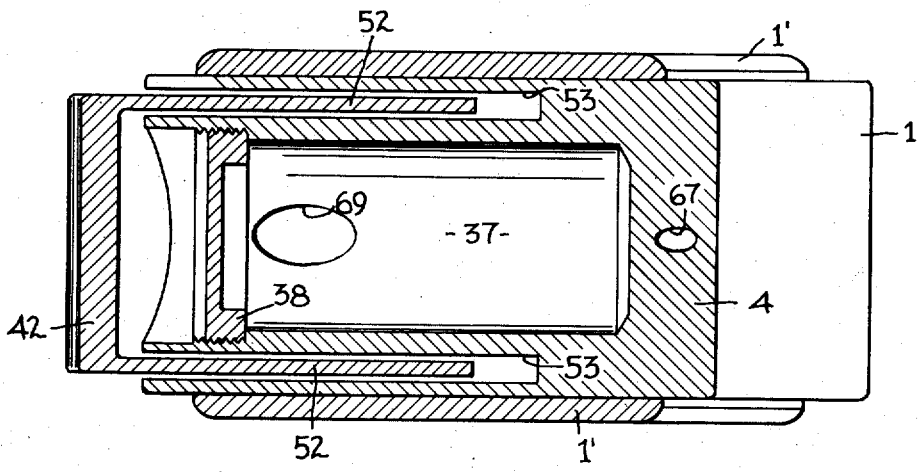
Fig. 6 is an enlarged transverse cross-sectional view of the fluid reservoir taken on line 6—6 of Fig. 2.

In order to prevent any inadvertent or accidental release of the plunger 6, means are provided to lock the plunger in its fully cocked position. For this purpose a circumferential recess 72 is provided on extension rod 15, which recess is formed at that longitudinal point on the rod where, when cocked, it first projects from, the cap 14. To the cap is pivotally secured as by screw 73, a locking disc or plate 74, which is best shown in Fig. 5. The plate 74 has a key-hole slot formed therein, which slot has a portion 75 of slightly greater diameter than the recessed portion 72 of rod 15, but of lesser diameter than the large diameter of the rod 15. The slot also has a portion 76 which is larger in diameter than the diameter of rod 15.

Two arcuate depressions 77 are formed in that surface of the locking disc which is contiguous to the cap 14, and a spring-pressed ball 78, which serves as a detent, is mounted in a cavity in the cap 14, and engages the depressions 77 to yieldably retain the disc in one or the other of two positions.

During the pumping action, the locking disc 74 is maintained in the dotted line position shown in Fig. 5, thereby permitting free longitudinal movement of the rod 15 through the slotted portion 76 of the disc. However, when the spring 19 has been fully compressed, the locking disc is rotated about screw 73 to the solid line position shown in Fig. 5, in which position, the slot portion 75 embraces the recessed portion 72 of rod 15 and prevents any relative longitudinal movement of the rod.

A longitudinally extending flat 79 is provided on the projecting threaded portion of the rod 15, and suitable index marks 80 are inscribed on the flat 79. In the instant case, four index marks are shown in Fig. 2 and each mark represents a plunger movement equivalent to one-eighth cc. of inoculant ejected. Thus, were the plunger 6 released with the adjusting nut 17 being in the position shown, a half cc. of inoculant would be ejected, as will hereinafter more fully appear. Similarly, were the adjusting nut 17 moved to the next adjacent mark 80, the ejecting movement of the plunger 6 would be arrested by abutment of nut 17 against locking disc 74 at a point corresponding to the ejection of ⅜ cc. of inoculant.

Figure 8:
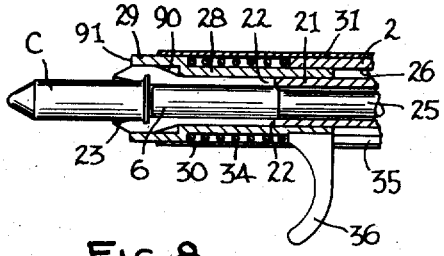
Fig. 8 is a fragmentary cross-sectional view similar to that of Fig. 2 but showing the cartridge in operative position in the injector device.

The cartridge or capsule which is utilized in connection with the instrument herein described is generally of the permanent or re-usable type and may be of a variety of shapes or sizes. However, the cartridge illustrated in Figs. 7 and 8 of the drawings, exemplifies a type of cartridge which could be satisfactorily used.

Figure 7:
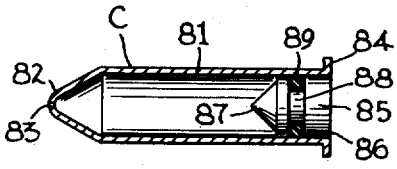
Fig. 7 is an enlarged longitudinal cross-sectional view of a form of ampule or cartridge which is ultilized in connection with the injector instrument.

Referring more particularly to Fig. 7 of the drawings, the cartridge C comprises a hollow cylindrical shell 81, the forward portion of which is conically tapered to a round nose 82 which is pierced by a small aperture 83, this aperture being approximately .003 inch in diameter.

The rearward portion of the shell 81 terminates in a radially outwardly extending circumferential flange 84 which is adapted to be received in the recess 24 in the collet jaws 23.

Slidably mounted in the shell 81 is a piston 85 having a flat rear face 86 and a conical front face 87. The piston 85 is provided with a circumferential recess 88 in which is retained a resilient sealing ring 89 which has wiping engagement with the wall of the shell.

The *medicament chamber or* cartridge C is filled with inoculant by removing the piston 85, and after the piston is replaced, the cartridge is ready for use.

In order to load the cartridge C in the injector instrument, the trigger 36 is retracted, causing the sleeve 28 to slide to the right, as viewed in Fig. 2, in opposition to the spring 34. This retractive movement causes the offset portion 29 of the sleeve to recede from the jaws 23 of the collet 21, whose inherent resiliency will cause the jaws to expand and open.

The cartridge C is then inserted in the collet with the flange portion 84 thereof in alignment with the recess 24.

It will be noted that the jaws 23 have an inclined or tapered external surface 90 which is engageable by the end 91 of the offset portion 29 of sleeve 28 when the jaws are expanded.

After the cartridge is inserted, the trigger 36 is released and the spring 34 returns the sleeve 28 to its initial position. This return movement of the sleeve causes the end 91 thereof to ride over the surface 90 and cam the jaws 23 into clamping relationship whereby the cartridge is firmly gripped.

After the nose 82 of the cartridge is properly positioned against the skin of the patient to be inoculated, the locking disc 74 is rotated to the non-locking position shown in dotted outline in Fig. 5, and the plunger 6 is released by depressing the button 62 on the valve stem 58.

The opening of the valve permits the hydraulic fluid to be released from the cylinder 10 by flowing through channel 66 into bore 57 of valve body 56 and thence through openings 64 into valve chamber 55. From chamber 55 the fluid returns to reservoir 37 through channel 68, thus reestablishing the supply of fluid in the reservoir.

Although movement of the plunger can be arrested by releasing button 62, thereby closing the valve, it is preferable that the adjusting nut 17 be so positioned as to stop the movement of the plunger when the desired amount of inoculant has been ejected.

The body of fluid in the cylinder 10 serves to cushion the forward movement of plunger 6 and therefore, the ejecting action is more sustained and less abrupt than would be the case were the movement entirely mechanical. This is a very desirable feature in such an instrument, not only because it permits better control over the jet inoculation process, but also because it reduces and minimizes the shock and wear and tear on the device itself, as well as on the cartridge.

It will be obvious that as the plunger 6 moves forwardly, it displaces the piston 85 in the cartridge C and causes the inoculant to be ejected *from the medicament chamber* in a high velocity jet through the opening 83.

As is apparent from the foregoing description, the cartridge C must be removed from the device after each injection and must be refilled and replaced for the succeeding injection. This method of operation is quite satisfactory under circumstances where the instrument is being utilized only occasionally or intermittently, as in treating patients singly in a hospital or doctor's office. However, there may be occasions when large groups of people must be inoculated rapidly, such as occurs in the inoculation of members of the armed forces. Under such circumstances, it is desirable that the time consumed in refilling and reloading the cartridge be minimized or eliminated entirely.

In Figs. 9 to 12 of the drawing, we have shown a modified form of an inoculant injector device which is particularly adapted for repeated or multiple shot operation for the rapid inoculation of large groups of people.

Except as hereinafter described, the instrument is constructed in accordance with the previously described embodiment shown in Figs. 1 to 8 inclusive.

In the modified form of injector device, the piston 11, plunger 6, and extension rod 15 are integrated into a single element having a bore 92 extending longitudinally therethrough. The extension rod 15 terminates in a threaded portion 93 of reduced diameter which forms a shoulder 94 on the rod 15.

The rod 15 projects through a cap 95 which is threadedly secured to the exterior of the piston housing 3 and which is provided with external screw threads 96. The cap is provided with spanner openings 97 to facilitate its assembly to the housing 3.

An internally threaded adjustable sleeve 98 having a circumferential flange 99 is threadedly secured to the cap 95, this sleeve having a central opening 100 to permit the rod 15 to pass therethrough. The flange 99 is slidably contained within another sleeve 101 which has threadedly secured thereto a disc 102 which in turn is secured to the portion 93 of rod 15 in abutment with the shoulder 94 thereof. The disc 102 is likewise provided with spanner openings 97.

Figures 9, 10, 11, 12:
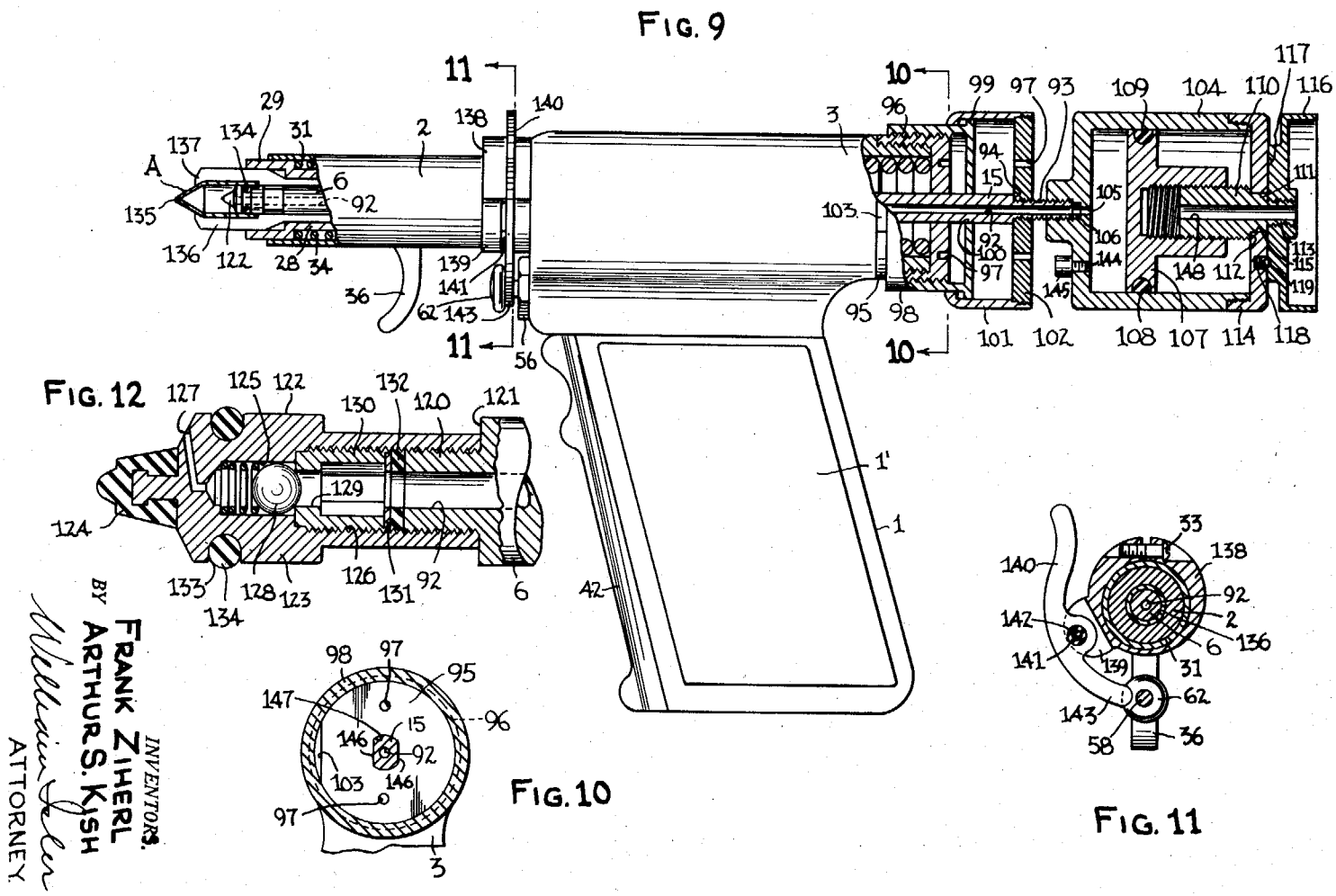
Fig. 9 is a side elevation of a modified form of the inoculant injector device as adapted for multiple shot operation, portions thereof being broken away to show details of the structure.
Fig. 10 is a fragmentary cross-sectional view taken on line 10—10 of Fig. 9.
Fig. 11 is a cross-sectional view taken on line 11—11 of Fig. 9.
Fig. 12 is an enlarged cross-sectional view of the plunger cap assembly shown in Fig. 9.

It will be apparent that as rod 15 moves to the left, as viewed in Fig. 9, the disc 102 will move into abutment with sleeve 99 and thereby will arrest or limit the movement of rod 15 and plunger 6. By rotating the sleeve 99 in a counterclockwise direction, it is caused to move longitudinally rearwardly and thereby will further curtail the stroke of the plunger 6. Thus, the stroke of plunger 6 can be adjusted by means of adjusting sleeve 99. In order that the length of stroke may be predetermined, the cap 95 has formed thereon a longitudinally extending flat 103 on which may be inscribed suitable indicia which, when correlated with the position of the forward edge of adjusting sleeve 99, will indicate, in terms of cubic centimeters or fractional parts of shots, the length of stroke of the plunger 6.

The sleeve 101 serves primarily as a guard to prevent the operator's hand or clothing from getting pinched between the disc 102 and the sleeve 99.

To the portion 93 of rod 15 is threadedly secured a syringe or reservoir body 104 which has an opening 105 in alignment with the bore 92 of rod 15. A resilient washer 106 is interposed between the end of rod 15 and body 104 in order to prevent leakage.

Slidably contained within the body 104 is a piston 107 which is provided with an annular recess 108 adapted to contain a resilient ring 109 having wiping engagement with the wall of the body 104. The piston is tapped to receive a threaded stem 110 having a portion 111 of reduced diameter thereby forming a shoulder 112. The stem terminates in a threaded portion 113.

The end of the reservoir body 104 is closed by means of a cap 114 which is threadedly secured to the body and which has a central opening 115 which serves as a bearing for the portion 111 of the stem 110.

A knob 116 is threadedly secured to the portion 113 of the stem and is utilized to rotate the stem 110 so as to move the piston 107 axially in one direction or the other. The face of the knob which lies adjacent the cap 114 is provided with a plurality of circumferentially spaced depressions 117, four equally spaced depressions being utilized in the embodiment shown. The cap 114 is provided with a cavity 118 containing a spring-pressed ball 119 which is adapted to successively engage the depressions 117 as the knob 116 is rotated. The detent action of the spring-pressed ball is utilized in a manner which will be described hereinafter.

The plunger 6, which extends through the barrel 2 of the instrument, terminates in a threaded portion 120 of reduced diameter, thereby forming a shoulder 121. On this threaded portion 120 is secured a plunger cap 122 which is shown in detail in Fig. 12.

The plunger cap 122 comprises a body 123 to which is integrated a resilient tip or nose 124. The body is bored as at 125 and is counterbored and tapped as at 126. A channel 127 leads from the bore 125 to the exterior of the body rearwardly of the nose 124.

A spring-pressed ball 128 is contained in the bore 125, and this ball seats against an opening 129 which is provided in a hollow-head screw 130 which is threadedly secured to the body in bore 126 thereof. A washer 131 and a resilient gasket 132 are interposed between the end of the portion 120 of the plunger 6 and the screw 130 in order to prevent leakage.

The body 123 is provided with an annular recess 133 in which is contained a resilient O-ring 134 which has wiping engagement with the internal wall of an ampule A of the type ordinarily utilized for inoculants. The ampule has a small opening 135 at the nose thereof.

Instead of the collet 21 described in the first-mentioned embodiment, we now utilize a self-opening collet 136, the jaws of which have inwardly extending flanges 137 which are adapted to embrace the forepart of the ampule A and hold it firmly in position. The collet is released by retraction of trigger 36 as hereinbefore described.

On the barrel 2 of the instrument, we have provided a split ring 138 having a slotted ear 139 projecting therefrom. The ring 138 serves the same function as the previously described ring 32, except that it also serves to retain a locking lever 140 which is pivotally secured thereto by means of a pin 141. A resilient sleeve 142 surrounds the pin 141 and serves to hold the lever in whatever position it is placed.

The lever is so located that its lower portion 143 will lie in the space intermediate the button 62 and the nut 56 so as to prevent the depressing of the valve stem 58. The lever 140 may be rotated clockwise, as viewed in Fig. 11, to release the button 62.

In utilizing the instrument for multiple-shot operation, the reservoir 104 must be filled with the inoculant which is to be injected. This may be accomplished in one of two ways. The reservoir, after removal from the rod 15, may have threadedly secured thereto an adapter (not shown) on which can be mounted a hypodermic needle. By rotation of the knob 116, the piston 107 is moved to the left, as viewed in Fig. 9, and the needle is then inserted in the bottle containing the liquid. The knob 116 is then counter-rotated and the consequent retraction of the piston 107 draws the inoculant into the reservoir body.

In lieu of the foregoing, the reservoir may be filled by pouring the inoculant into the body 104 through an opening 144 which is ordinarily sealed by a threaded plug 145.

After the reservoir has been filled, it is assembled to the rod 15. In order to prevent the rod 15 from rotating during the assembly operation, the rod has two oppositely disposed plane surfaces 146 formed thereon, which surfaces extend longitudinally thereof for a portion of its length. As seen in Fig. 10, the central opening 147 in cap 95 conforms to the shape of the rod 15 and thereby prevents axial rotation thereof.

In order to fill the *chamber or* ampule A with inoculant, the plunger 6 is first retracted by the pumping of handle 42, as heretofore described. The instrument is then pointed upwardly and the knob 116 is rotated until the inoculant comes out of the opening 135 in the ampule A. In order to prevent the stem 110 from becoming airbound in the piston 107, the stem is provided with a bore 148 which serves to vent any entrapped air.

With the ampule A thus filled, the adjusting sleeve 98 is set to give the desired stroke of plunger 6, that is, one shot, a half shot, etc.

The locking lever 140 is then rotated to release position, and the button 62 is depressed thereby releasing the plunger 6 and causing the plunger cap 122 to move forwardly in the ampule and eject the inoculant. As the plunger cap reaches the end of its stroke, the nose 124 thereof becomes wedged in the nose of the ampule and seals the opening 135, thus preventing any drip or leakage from the ampule after the shot has been completed. *The engagement of the nose 124 also blocks or prevents any transfer of inoculant from the reservior to the ampule which might inadvertently be attempted after the forward movement of the plunger has been completed.*

During the forward movement of the plunger cap, the back pressure on the fluid in channel 127 and bore 125 causes the ball 128 to seat on the screw 130 and prevents any rearward flow of the fluid.

In order to repeat the inoculating shot, the plunger 6 is again retracted by means of manipulation of the handle 42 and the lock lever 140 is rotated to the safety or locking position. The instrument is again pointed upwards and the knob 116 is rotated one click (one-fourth revolution), two clicks (one-half revolution), etc., as desired. Inasmuch as the bore 92 is now full of inoculant, the movement of piston 107 causes the ampule A to receive an amount of fluid which corresponds to the volume displaced by the piston. The piston will, of course, move longitudinally an exact distance for each full or fractional revolution of the knob 116. Therefore the quarter-turns of the knob can be correlated to the movement of the piston 107 so as to denote the quantity of inoculant which is going into the ampule. Thus, one click may denote one-eighth cubic centimeter or one-half shot; two clicks, one-fourth cc. or a full shot; etc.

The syringe or reservoir 104 may have a capacity of, for example, 20 cc., and if one shot requires ½ cc., it will be apparent that about 40 inoculator shots can be given with the instrument before having to refill it.

Thus it will be apparent that the rapid inoculation of large groups of people is made possible by the self-loading characteristics of our invention.

The instrument may also be used for single shot operation using standard ampules, in which case the syringe assembly is not required as the ampule is replaced after each shot.

The adjusting sleeve 98, which determines the length of stroke of the plunger 6, is utilized primarily for single shot operation. The metering of the fluid by means of the knob 116 is used solely for multiple shot operation.

Thus we have provided an inoculant injector instrument which in all respects meets the objectives hereinbefore set forth.

It is to be understood that the forms of our invention, herewith shown and described, are to be taken as preferred examples of the same, and that various changes in the shape, size and arrangement of parts may be resorted to, without departing from the spirit of our invention or the scope of the subjoined claims.

Having thus described our invention, we claim:

1. In an injector instrument, the combination of a cylinder, a piston slidably mounted in said cylinder, a fluid pump communicating with said cylinder and effective to cause displacement of said piston, a spring engaging said piston and energizable in response to said displacement of said piston, a plunger secured to said piston and movable therewith, an inoculant-charged body disposed in the path of movement of said plunger, and valve means communicating with said cylinder and operable to recirculate the fluid from said cylinder to said pump and release the pressure in said cylinder whereby said plunger is displaced by the action of said spring.

2. A combination, as defined in claim 1, in which a movable extension rod is secured to said piston, which rod projects exteriorly of said cylinder, and locking means are provided exteriorly of said cylinder for selectively securing said rod against movement, whereby said plunger is immobilized.

3. A combination, as defined in claim 1, in which a movable extension rod is secured to said piston, which rod projects exteriorly of said cylinder, and adjustable stop means are provided on said rod for limiting the movement of said rod in response to action of said spring, whereby corresponding movement of said plunger is restricted.

4. In an injector instrument, the combination of a cylinder, a piston slidably mounted in said cylinder, a spring engaging said piston, a plunger secured to said piston and movable therewith, an inoculant-charged body disposed in the path of movement of said plunger, a fluid reservoir provided in said instrument, a pump communicating with said reservior, said pump being operable to force fluid from said reservoir into said cylinder whereby said piston is retracted in opposition to said spring, and means for selectively releasing said fluid from said cylinder and recirculating it to said reservoir whereby said plunger is actuated by said spring.

5. A combination, as defined in claim 4, wherein said means comprise a channel interconnecting said cylinder and said reservoir, and a normally closed valve interposed in said channel.

6. A combination, as defined in claim 4, wherein an extension rod is secured to said piston and movable therewith, which rod extends exteriorly of said cylinder, and adjustable stop means are provided on said rod for limiting the spring-actuated movement of said rod whereby corresponding movement of said plunger is restricted.

7. A combination, as defined in claim 6, wherein locking means are provided exteriorly of said cylinder for selectively securing said rod against movement and thereby immobilizing said plunger.

8. In an injector instrument, the combination of a cylinder, a piston slidably mounted in said cylinder, a plunger secured to said piston and movable therewith, an inoculant-charged body disposed in the path of movement of said plunger, spring means engaging said piston, fluid pressure-producing means communicating with said cylinder and adapted to retract said piston in opposition to said spring, manually operable means for actuating said pressure-producing means, whereby said plunger may be retracted, and valve means for selectively releasing the fluid from said cylinder and recirculating it to said pressure-producing means, whereby said plunger is displaced by action of said spring.

9. In an injector instrument, the combination of a cylinder, a plunger movable in said cylinder, an inoculant-charged body supported in alignment with said cylinder, spring means in said cylinder for advancing said plunger into said body to discharge the contents thereof, and fluid pressure means carried by said instrument, including a pump, for forcing fluid into said cylinder to retract said plunger in oposition to said spring means, whereby said spring means is put under compression.

10. In an injector instrument, the combination of a cylinder, a piston movable in said cylinder, a plunger secured to said piston for movement therewith, an inoculant-charged body supported in alignment with said cylinder, spring means engaging the plunger for advancing said plunger into said body to discharge the contents thereof, and fluid pressure means carried by said instrument, including a pump, for forcing fluid into said cylinder to retract said piston and plunger in opposition of said spring means, whereby said spring means is put under compression.

11. In an injector instrument, the combination of a cylinder, a piston movable in said cylinder, a plunger secured to said piston and movable therewith, an inoculant-charged body supported in alignment with said cylinder, spring means engaging the plunger for advancing said plunger into said body to discharge the contents thereof, fluid pressure means carried by said instrument, including a pump, for forcing fluid under pressure into said cylinder to retract said piston and plunger in opposition to said spring means, whereby said spring means is put under compression, and valve means for selectively recirculating said fluid from said cylinder to said pump.

12. In an injector instrument, the combination of a hollow plunger, means for retracting said plunger, [an ampule] *a medicament chamber* disposed in axial alignment with said plunger, metering means for feeding a predetermined volume of liquid into said [ampule] *chamber* through said plunger, means for advancing said plunger into said [ampule] *chamber* to eject the liquid therefrom, and a resilient nose on said plunger, adapted to engage said [ampule] *chamber* upon completion of the stroke of said plunger, whereby to seal said [ampule] *chamber* against further discharge of liquid.

13. In an injector instrument, the combination of a hollow plunger, means carried by said instrument for retracting said plunger, [an ampule] *a medicament chamber* supported in alignment with said plunger, a liquid reservoir carried by said instrument communicating with said plunger, a piston movable in said reservoir, [rotatable] *movable* means [secured to] *engaging* said piston for advancing said piston [a predetermined distance per revolution thereof] to feed liquid into said [ampule] *chamber* through said plunger, and means forming part of the instrument for advancing said plunger to discharge said liquid from said [ampule] *chamber*.

14. A combination, as defined in claim 13, wherein said [rotatable] *movable* means comprises a *rotatable* threaded element engaging said piston.

15. A combination, as defined in claim 14, wherein said threaded element is provided with indicating means for determining the relative angular rotation thereof.

16. In an injector instrument, the combination of a cylinder, a hollow plunger movable in said cylinder, a hollow body adapted to contain inoculant supported in alignment with said plunger, metering means on the instrument associated with said plunger for feeding inoculant into said body through said plunger, spring means engaging the plunger for advancing said plunger into said body to discharge the contents thereof, and fluid pressure means carried by said instrument communicating with said cylinder to retract said plunger in opposition to said spring means, whereby said spring means is compressed.

*17. In an injector instrument, the combination of a hollow body, a medicament chamber having a discharge opening therein disposed adjacent one end of said body, ejection means carried by said body and movable toward said chamber to discharge medicament therefrom, a medicament reservoir, means providing a passageway between said reservoir and said chamber, means movable relatively to said reservoir for transferring medicament from said reservoir to said chamber through said passageway, and actuating means carried by said instrument and cooperable with said ejection means to effect discharging movement thereof.*

*18. A combination, as defined in claim 17, including means for sealing said passageway in response to discharging movement of said ejection means.*

*19. In an injector instrument the combination of a hollow body, a medicament chamber having a discharge opening therein disposed adjacent one end of said body, ejection means carried by said body and movable toward said chamber to discharge medicament therefrom, a medicament reservoir, means providing a passageway between said reservoir and said chamber, means movable relatively to said reservoir for transferring medicament from said reservoir to said chamber through said passageway, actuating means associated with said ejection means for advancing said ejection means toward said chamber, and force-compounding means connected to said actuating means to effect energization thereof.*

References Cited in the file of this patent or the original patent

UNITED STATES PATENTS

| | | |
|---|---|---|
| 411,375 | Cooke | Sept. 17, 1889 |
| 1,118,040 | Mulder | Nov. 24, 1914 |
| 1,144,343 | Benmosche et al. | June 29, 1915 |
| 1,569,457 | Carstens | Jan. 12, 1926 |
| 2,047,010 | Dickinson | July 7, 1936 |
| 2,295,849 | Kayden | Sept. 15, 1942 |
| 2,322,245 | Lockhart | June 22, 1943 |
| 2,374,368 | Mejia | Apr. 24, 1945 |
| 2,413,303 | Folkman | Dec. 31, 1946 |
| 2,550,163 | Phenning | Apr. 24, 1951 |
| 2,635,601 | May | Apr. 21, 1953 |
| 2,653,604 | Hein | Sept. 29, 1953 |
| 2,687,724 | Ziherl et al. | Aug. 31, 1954 |

FOREIGN PATENTS

| | | |
|---|---|---|
| 102,221 | Australia | Oct. 7, 1937 |
| 505,931 | France | Aug. 10, 1920 |
| 624,958 | Great Britain | June 20, 1949 |